United States Patent
Luleci

(10) Patent No.: US 11,103,337 B2
(45) Date of Patent: Aug. 31, 2021

(54) ARTIFICIAL SPHINCHTER

(71) Applicant: Huseyin Luleci, Istanbul (TR)

(72) Inventor: Huseyin Luleci, Istanbul (TR)

( * ) Notice: Subject to any disclaimer, the term of this patent is extended or adjusted under 35 U.S.C. 154(b) by 247 days.

(21) Appl. No.: 16/481,839

(22) PCT Filed: Feb. 27, 2017

(86) PCT No.: PCT/TR2017/050076
§ 371 (c)(1),
(2) Date: Jul. 30, 2019

(87) PCT Pub. No.: WO2018/156092
PCT Pub. Date: Aug. 30, 2018

(65) Prior Publication Data
US 2019/0374324 A1    Dec. 12, 2019

(51) Int. Cl.
*A61F 2/00*    (2006.01)
(52) U.S. Cl.
CPC ...... *A61F 2/004* (2013.01); *A61F 2250/0003* (2013.01)
(58) Field of Classification Search
CPC ...... A61F 2/004; A61F 2/0031; A61F 2/0036; A61F 2/0054; A61F 2/0013; A61F 2/0004; A61F 2/0027
See application file for complete search history.

(56) References Cited

U.S. PATENT DOCUMENTS

| 4,222,377 A | | 9/1980 | Burton | |
| 4,386,601 A | * | 6/1983 | Trick | A61F 2/0027 |
| | | | | 128/DIG. 25 |
| 5,478,305 A | * | 12/1995 | Craggs | A61F 2/004 |
| | | | | 600/31 |

FOREIGN PATENT DOCUMENTS

| EP | 0409592 A1 | 1/1991 |
| EP | 3030196 A1 | 6/2016 |
| GB | 2174911 A | 11/1986 |

* cited by examiner

*Primary Examiner* — John P Lacyk
(74) *Attorney, Agent, or Firm* — Bayramoglu Law Offices LLC

(57) ABSTRACT

An artificial sphincter including an inflatable occlusion means for occluding a body passage, a stretchable fluid reservoir and a pump means. The pump means has a first port in fluid communication with the occlusion means and a second port in fluid communication with the fluid reservoir for selectively transferring an isotonic fluid from the occlusion means to said reservoir to deflate said occlusion means. The artificial sphincter further includes a pressure compensation balloon which is attached to the fluid reservoir and which, in use, is to be implanted in the abdomen of a patient.

12 Claims, 7 Drawing Sheets

Figure 1:
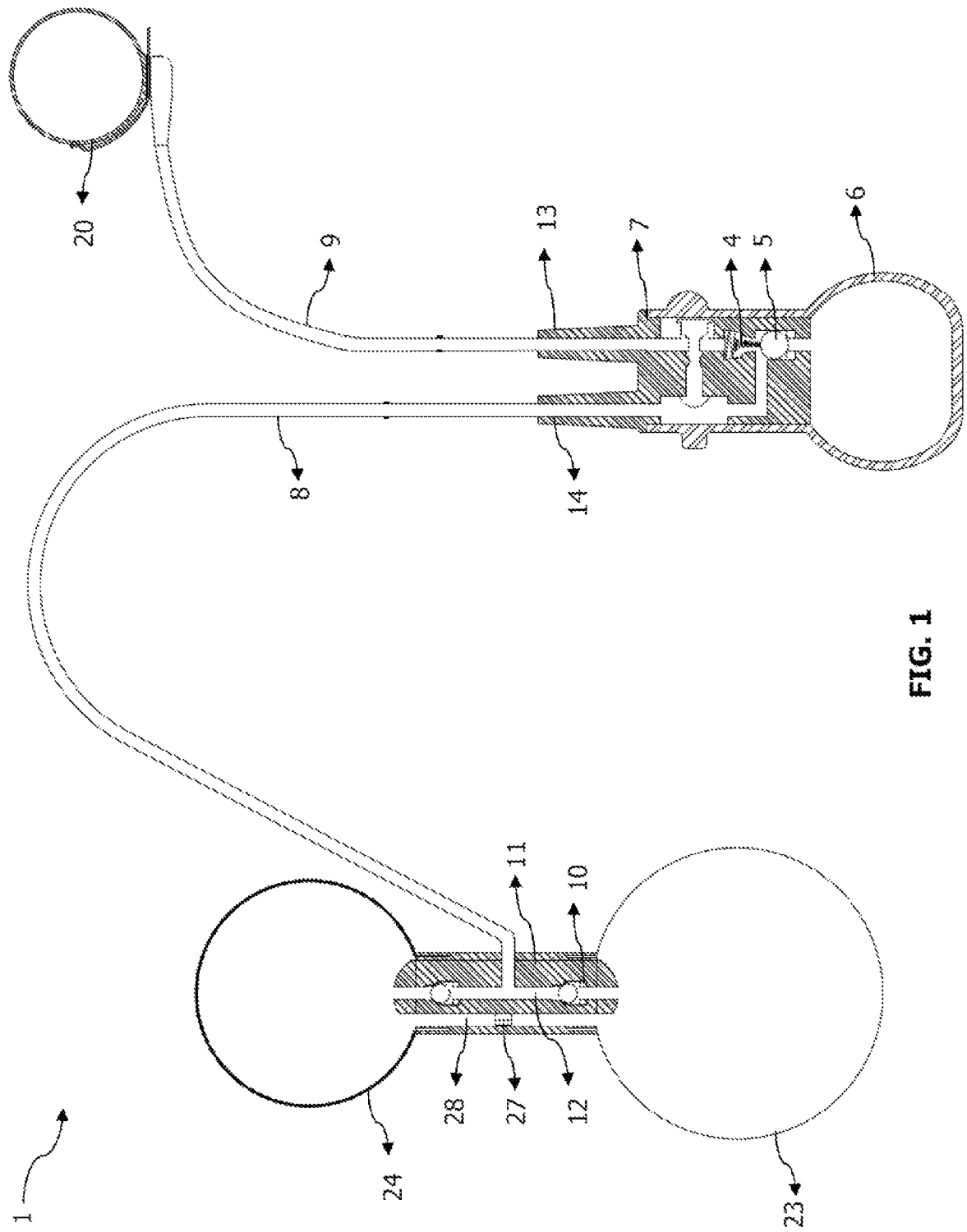

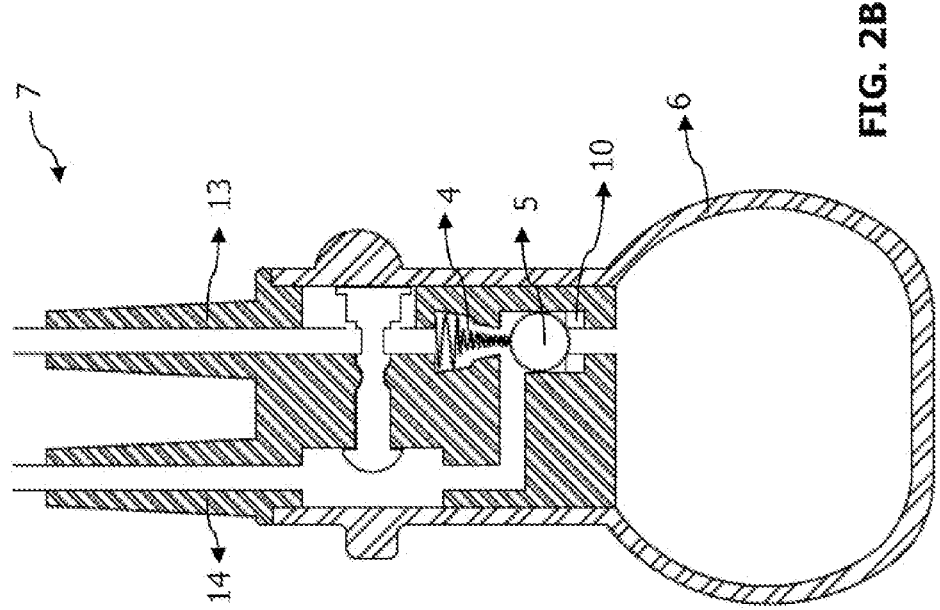
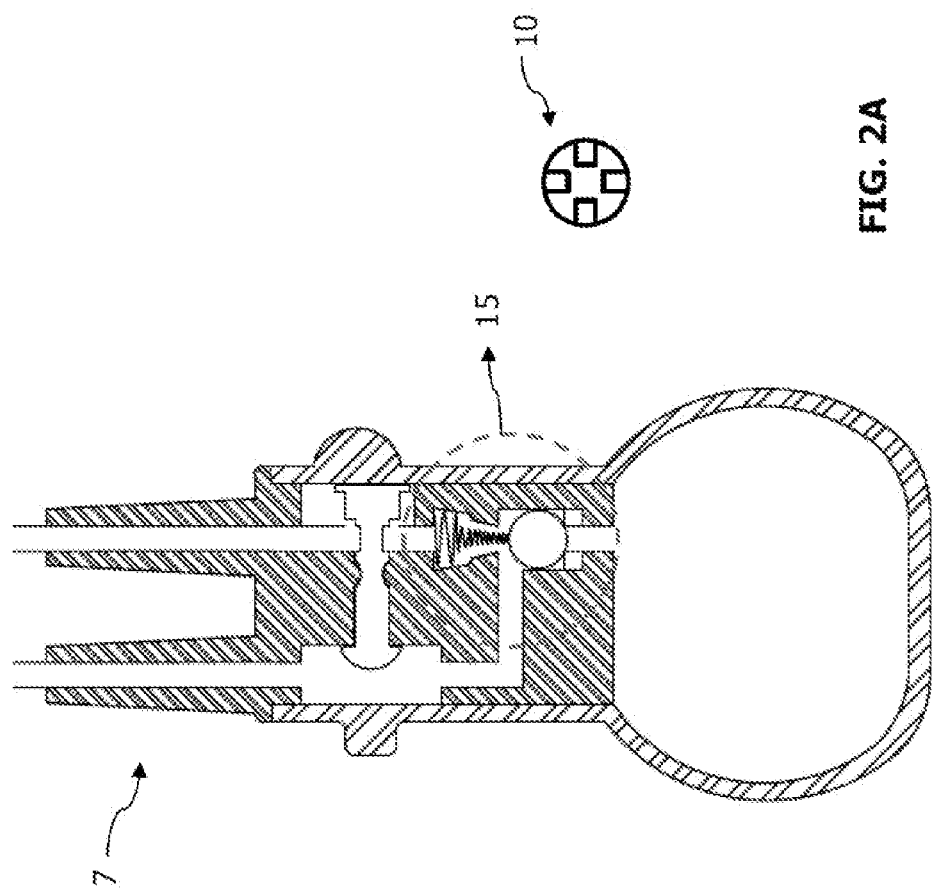

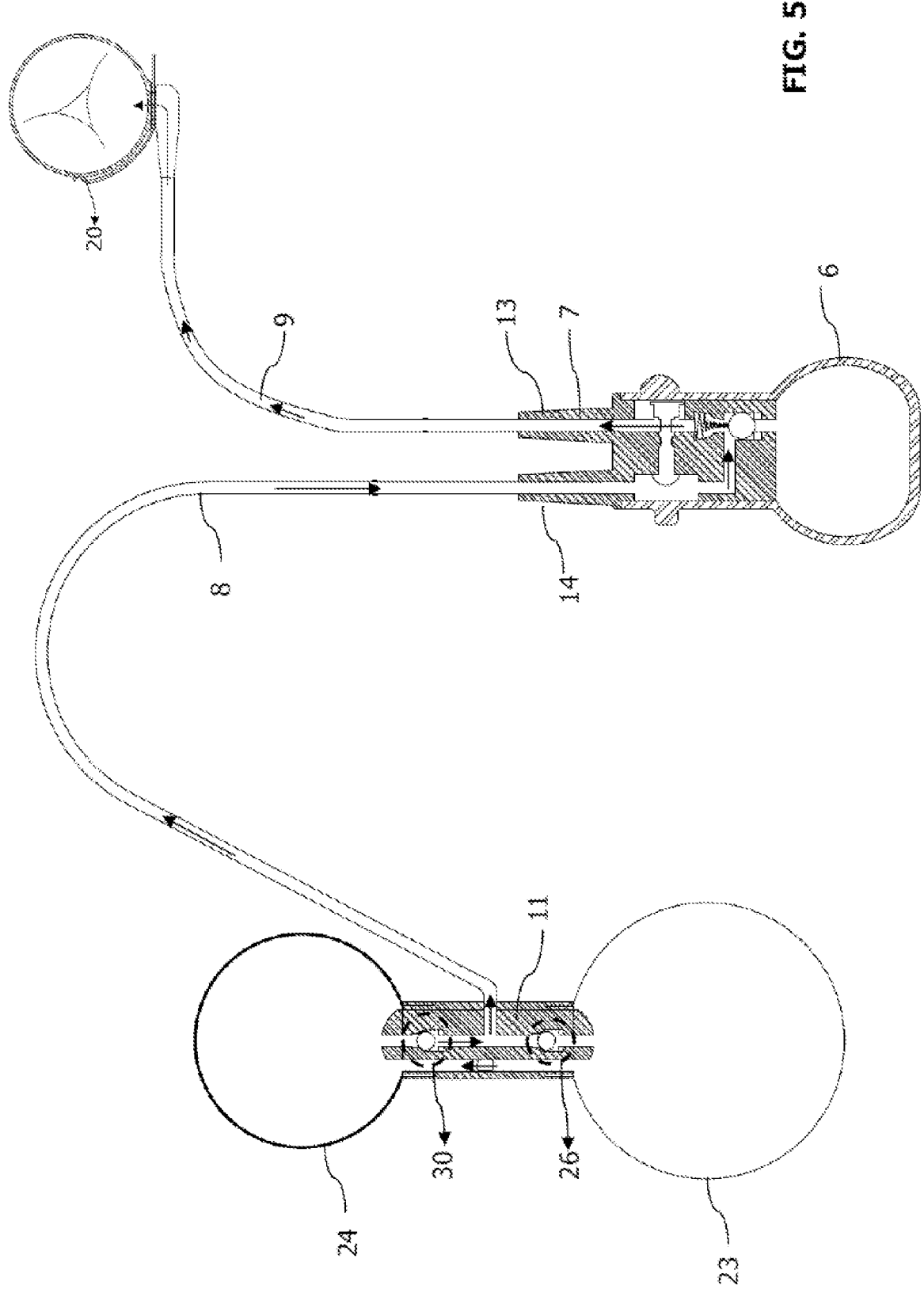

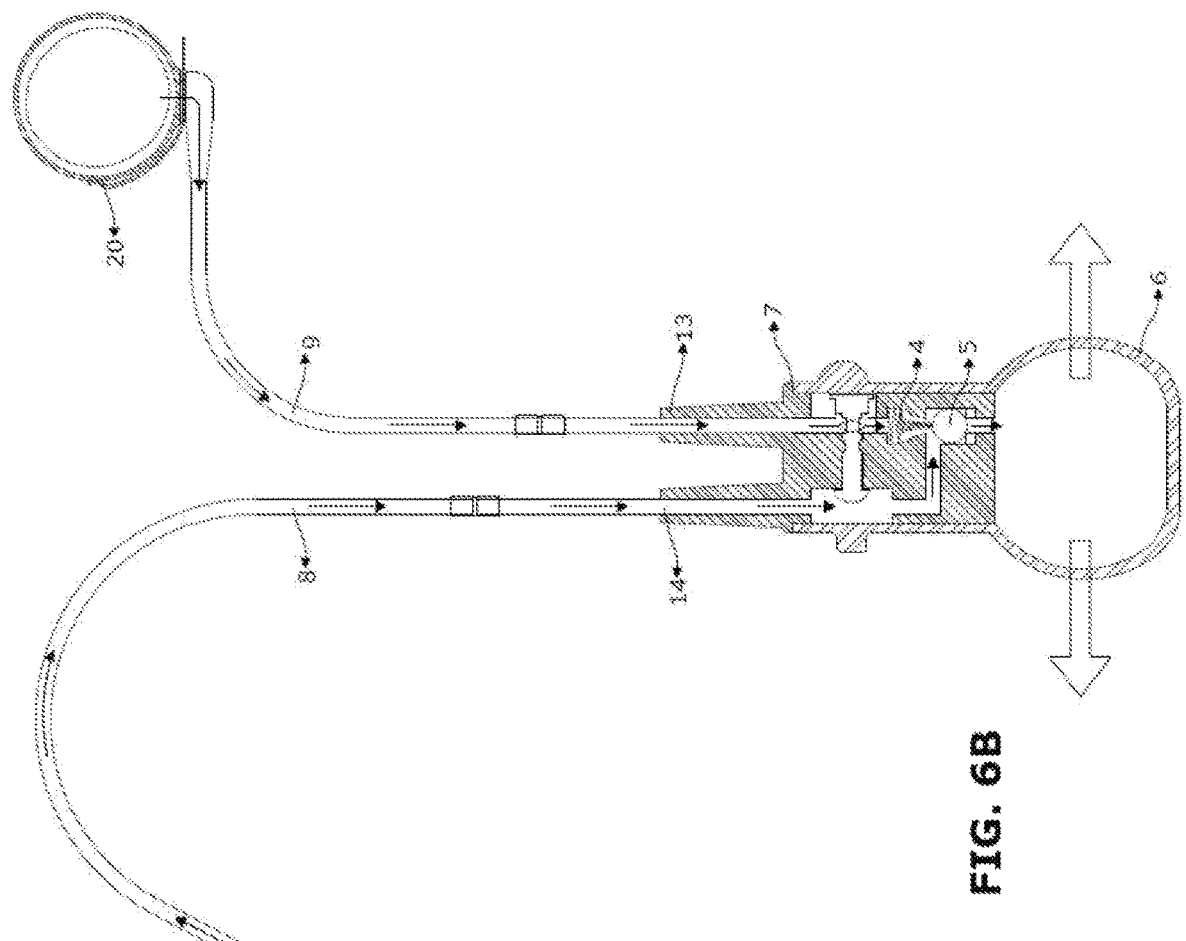
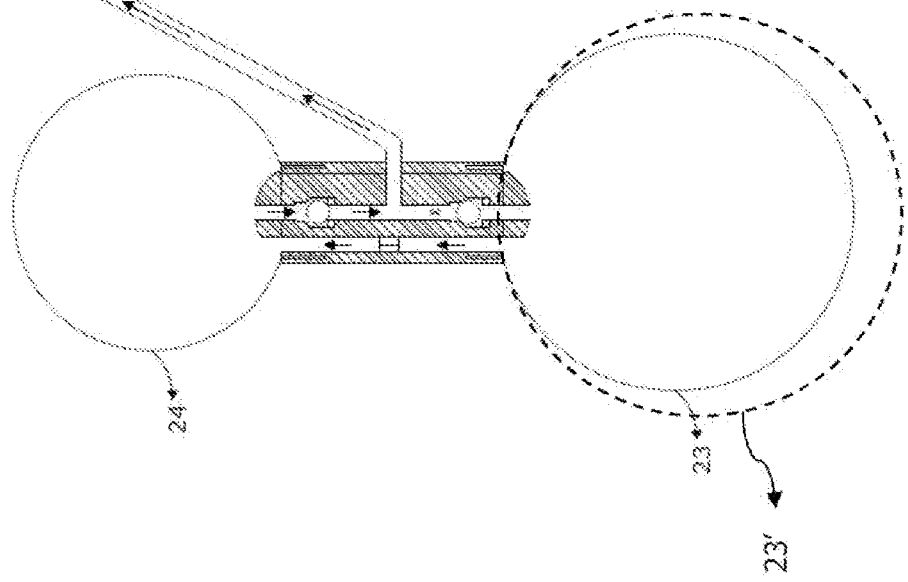
FIG. 6B

US 11,103,337 B2

ARTIFICIAL SPHINCHTER

CROSS REFERENCE TO THE RELATED APPLICATIONS

This application is the national phase entry of International Application No. PCT/TR2017/050076, filed on Feb. 27, 2017, the entire contents of which are incorporated herein by reference.

TECHNICAL FIELD

The present invention generally relates to an apparatus for treating incontinence and more specifically relates an apparatus for providing an inflatable artificial sphincter for control of excretory body passages. The invention provides a novel solution which effectively occludes excretory body passage of a patient even when a sudden pressure increment occurs in the abdomen of a patient to which an artificial sphincter is implanted.

BACKGROUND

A biological urinary sphincter prevents urinary flow via mucosal coaptation, compression and pressure transmission. On the other hand, an artificial urinary sphincter mimics the biological urinary sphincter by providing a competent bladder outlet during urinary storage and an open unobstructed outlet to permit voluntary urination. Similarly, an artificial rectal sphincter may be used to treat fecal incontinence caused by neurological or muscular dysfunction of an anal sphincter.

A known treatment for some cases of incontinence is to provide a patient with a mechanism to occlude the affected excretory body passage. These mechanisms are typically surgically implanted within the patient's body and are adapted to be operable by the patient to selectively open and occlude the body passage. Inflatable artificial sphincters are well known devices in the state of the art. Inflatable sphincters typically include an inflatable cuff for surrounding the passage to be occluded. Usually a pump cooperatively associated with a fluid reservoir is utilized to transfer fluid into and out of the cuff. As fluid is transferred into the cuff, the cuff inflates and closes the circumscribed body passage.

Artificial urinary sphincters known in the state of the art consist of three major parts, namely the fluid reservoir, the cuff and a pump which is usually designated as the control mechanism of the AUS. The pump can be placed in a man's scrotum. It can also be placed underneath the skin in a woman's lower belly, labia or leg. Two conduit tubes connect all three major parts to each other. Use of an extra element, in particular of a conduit tube, increases the implantation time, complexity of the surgery and most importantly, the infection risk of a patient after implantation within the body.

EP 3,030,196 A1 discloses an entirely implantable device for occluding the urethra or bladder neck utilizing an occlusive cuff connected to a control mechanism via a conduit tube. The occlusive cuff is reversibly changed from an activated occlusive condition to a deactivated non-occlusive condition by depressing a deactivation button contained within a resilient, elastomeric sheath surrounding the control mechanism. Those skilled in the art usually designate this type of occlusion means as AUS, standing for Artificial Urinary Sphincters.

A known problem with the inflatable artificial sphincters existing in the state of the art is the failure of the cuff in effectively occluding the excretory body passage when a sudden pressure increase occurs in the patient's abdomen. A sudden pressure increase may occur when, for instance, the patient laughs, coughs or is burst into laughter and also by way of certain physical movements such as bending the upper body down or when lifting a weight. In such cases, the normal pressure formed in the inflatable cuff may fail to effectively occlude the excretory body passage and excreted fluid which already accumulated behind the cuff or in the bladder may unintentionally leak outside the patient's body.

SUMMARY

Primary object of the present invention is to provide a new artificial sphincter which eliminates the drawbacks of the existing artificial sphincters.

In particular, an object of the present invention is to provide a new control mechanism for an artificial sphincter which effectively occludes the excretory body passage of a patient even when a sudden pressure increase occurs in the abdomen of the patient.

A further object of the present invention is to provide a new artificial sphincter which is simple and easy to implant in the body of patient suffering incontinence.

A final object of the present invention is to provide a novel artificial sphincter which is responsive to abdominal pressure changes and which does not require implantation of an extra conduit to the occlusion means. In this context, infection risks and implantation time are reduced and a non-complex artificial sphincter is obtained.

BRIEF DESCRIPTIONS OF THE DRAWINGS

The figures whose brief explanations are herewith provided are solely intended for providing a better understanding of the present invention and are as such not intended to define the scope of protection or the context in which said scope is interpreted in the absence of the description.

Figure 4A:
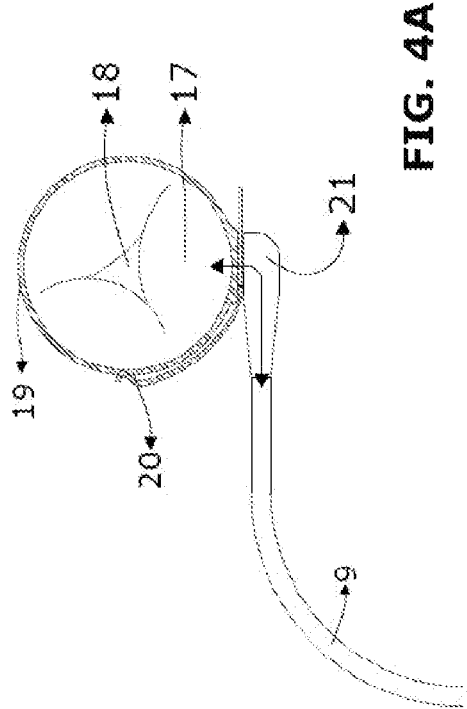
Figure 4B:
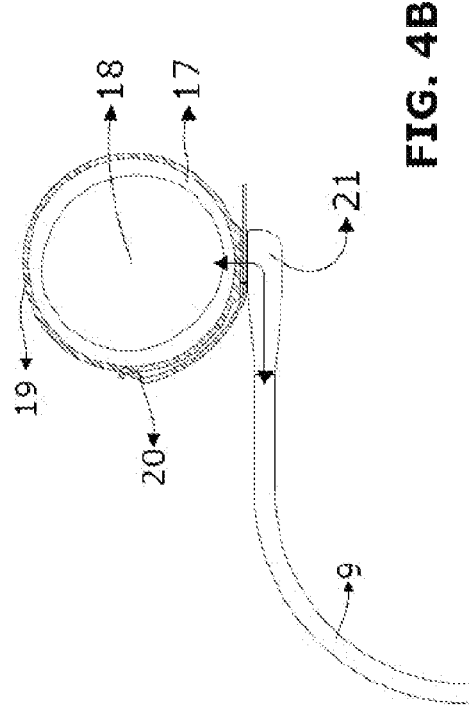
Figure 3:
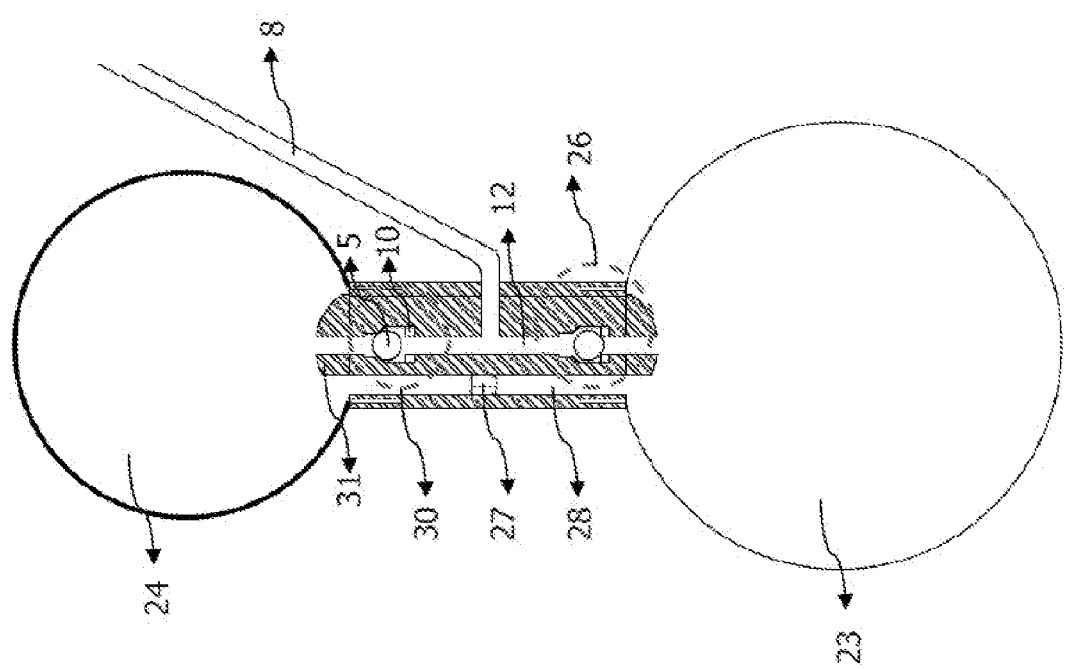
Figure 6A:
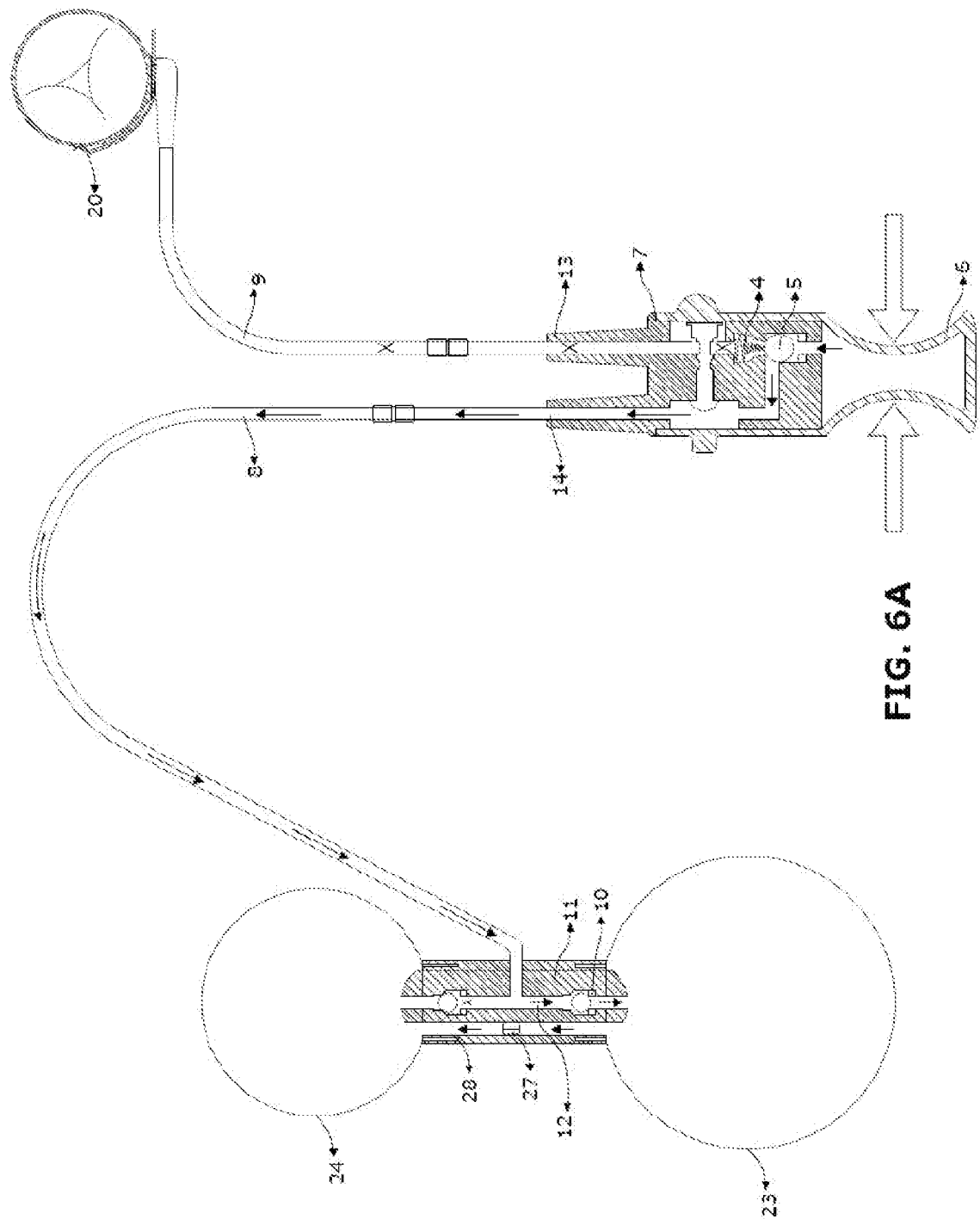
Figure 8:
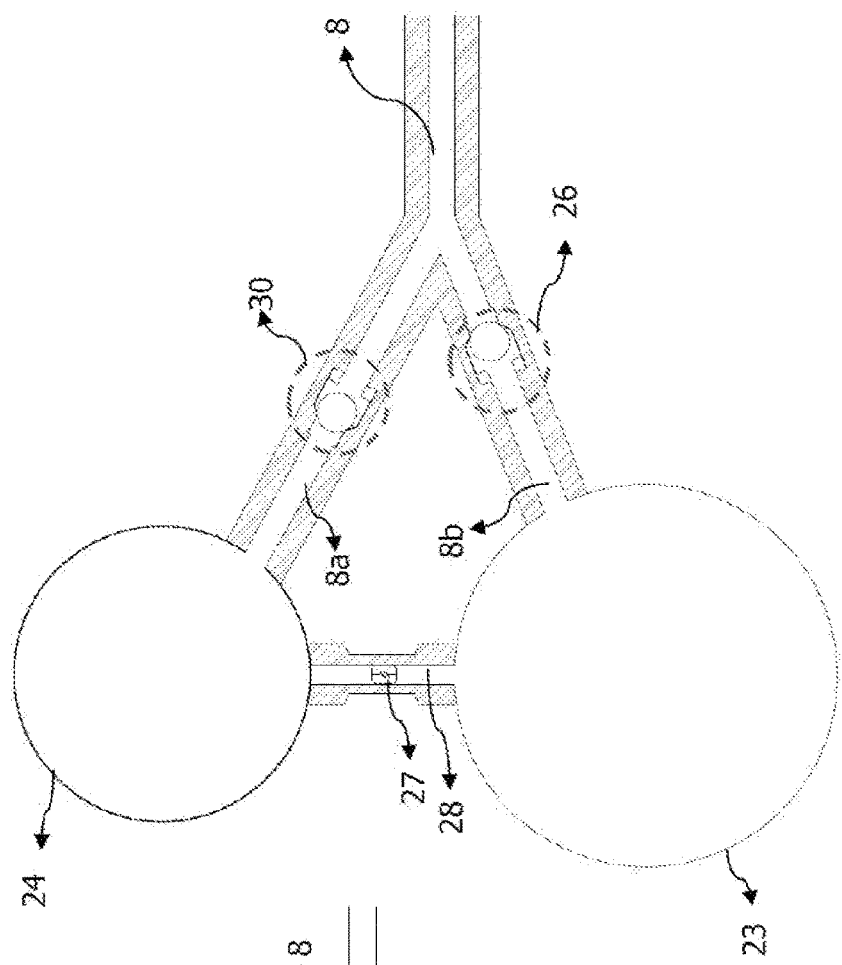
Figure 7:
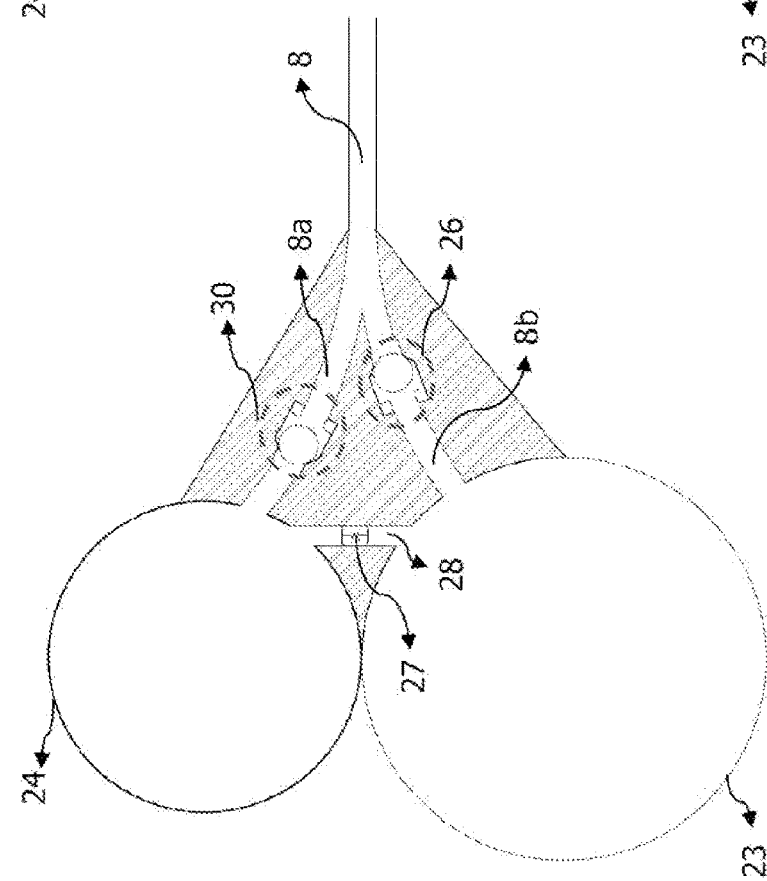

FIG. 1 shows a schematic view of an artificial sphincter according to the present invention, FIG. 2A and FIG. 2B show the cross sectional view of the pump of the artificial sphincter according to the present invention, FIG. 3 shows the cross sectional view of the reservoir and the pressure compensating balloon of the artificial sphincter, FIG. 4A shows 2D view of a cuff in which the urethral passage is in occluded condition, FIG. 4B shows 2D view of a cuff in which the urethral passage is in open condition, FIG. 5 shows the flow stream of the fluid contained in the artificial sphincter during a moment of sudden pressure increase in the abdomen of a patient, FIG. 6A shows the flow stream of the fluid contained in the artificial sphincter during the first step of deflation of the occlusion means, FIG. 6B shows the flow stream of the fluid contained in the artificial sphincter during the second step of deflation of the occlusion means FIG. 7 shows the fluid reservoir and the pressure compensation balloon in the second embodiment of the present invention, FIG. 8 shows the fluid reservoir and the pressure compensation balloon in the third embodiment of the present invention,

DETAILED DESCRIPTION OF THE EMBODIMENTS

The list of reference numerals used in the appended drawings is as follows;

1 artificial sphincter
4 spring
5 ball
6 pump bulb
7 pump
8 second tube
8a first branch
8b second branch
9 first tube
10 pervious seat
11 connecting element
12 distribution conduit
13 first port
14 second port
15 three way valve
17 inflatable cushion
18 body passage
19 sheath
20 occlusion means
21 cuff lock
23 Reservoir
24 Pressure compensation balloon
26 second check valve
27 flow retarder
28 flow passage
30 first check valve
31 protrusion Objects of the present invention are achieved by the features of claim 1 in which an artificial sphincter (1) according to the present invention comprises an inflatable occlusion means (20) for occluding a body passage, a stretchable fluid reservoir (23) and a pump means (7) having a first port (13) in fluid communication with the occlusion means (20) and a second port (14) in fluid communication with the fluid reservoir (23) for selectively transferring an isotonic fluid from the occlusion means to the fluid reservoir in order to deflate the occlusion means so that the body passage may be opened. As illustrated in FIG. 1, the artificial sphincter (1) of the present invention further comprises a pressure compensation balloon (24), which is in fluid communication with said fluid reservoir via a flow passage (28) and which, in use, is to be implanted in the abdomen of a patient. A first check valve (30) blocks fluid flow from the second port (14) of the pump means (7) towards said pressure compensation balloon (24). A second check valve (26) blocks fluid flow from the fluid reservoir (23) towards the pressure compensation balloon (24). Hence, the fluid contained in the pressure compensation balloon is freely flowable towards the inflatable occlusion means and, in use, a pressure increase which occurs in the abdomen of a patient can be instantly conveyed to the inflatable occlusion means.

In the first embodiment, the pressure compensation balloon (24) is attached to the fluid reservoir via a connection element (11). As shown in FIG. 3, the connection element (11) has a distribution conduit (12) which has, at its first end, a first check valve (30) blocking fluid flow into said pressure compensation balloon (24) and which has, at its second end, a second check valve (26) blocking fluid flow from said reservoir to said pressure compensation balloon. The connection element has a flow passage (28) allowing fluid flow from the fluid reservoir to the pressure compensation balloon. The distribution conduit (12) is in fluid communication with the second port (14) of the pump means so that the fluid contained in the pressure compensation balloon is freely flowable towards said inflatable occlusion means and, in use, a pressure increase which occurs in the abdomen of a patient is instantly conveyed to said inflatable occlusion means.

A sudden pressure increase in the abdomen of a patient occurs usually when the patient coughs, laughs or lifts a heavy object. As classical artificial sphincters apply a constant pressure in the inflatable occlusion means, known artificial sphincters fail to effectively occlude the body passage during said sudden pressure increase. In such a case, urine already accumulated in the bladder of the patient undesirably leaks outside the body of the patient, usually leading the patient feel ashamed in the society. The artificial sphincter (1) according to the present invention offers a new solution in which the sudden pressure increase is felt or noticed by a pressure compensation balloon (24) located in the in the abdomen and is instantly transmitted to the inflatable occlusion means (20) so that an undesirable leakage of urine is prevented.

As well known by those skilled in the art, pressure in a liquid medium propagates with the speed of sound under ideal conditions. Hence, any sudden increase in the internal pressure of the abdomen of a patient is immediately transferred to the occlusion means (20) via a pathway through which the isotonic fluid is freely flowable towards the occlusion means. Hence, the pressure of the occlusion means suddenly increases in order to effectively occlude the body passage (18) during the moment of sudden abdominal pressure increase.

FIG. 2A and FIG. 2B show the cross sectional view of the pump means (7) of the artificial sphincter (1) according to the present invention. The pump means (7) has a first port (13) in fluid communication with said occlusion means (20) and a second port (14) in fluid communication with said fluid reservoir (23) for selectively transferring isotonic fluid from said occlusion means to said reservoir to deflate said occlusion means so that the body passage (18) may be opened. The body passage is opened, as shown in FIG. 4B, when the patient intends to urinate or defecate. The term port is used to indicate a node through which fluid exchange may be made in between the occlusion means and the fluid reservoirs.

As illustrated in FIG. 2A and FIG. 3, the first check valve (30) or the second check valve (26) located in distribution conduit (12) may have pervious seat (10) and a ball (5) which allows fluid flow when the fluid forces said ball towards said pervious seat (10) and which blocks fluid flow when the flow direction of the fluid is reversed. The pervious seat (10) may have a plurality of pillars and gaps in between said plurality of gaps so that fluid may pass through the gaps. While the pervious seat (10) is at one side of the ball (5), a converging canal shall be formed on the other or opposite side of the ball (5) so that the ball, under effect of the reverse fluid flow, moves towards the converging canal and clogs the canal. The three way valve (15) of the pump means (7) may have a similar design having a pervious seat (10) and a ball (5) which allows fluid flow when the fluid forces said ball towards said pervious seat (10) and which blocks fluid flow when the flow direction of the fluid is reversed.

As shown in FIG. 4A and FIG. 4B, the occlusion means (20) has an inflatable cushion (17) having a body passage (18). Usually, the occlusion means is designated as a cuff which has an inflatable cushion (17) affixed onto the sheath (19) which is non-extendible. In use, the inflatable cushion (19) is implanted such that it surrounds the urethra or rectal canal of a patient and when inflated, occludes the body passage. As the sheath (19) surrounding the inflatable cushion (17) does not stretch, the inflatable cushion (17) occludes the body passage (18) formed in the central area of the inflatable cushion.

The pump means (7) has a bulb (6) which contains isotonic fluid and which transfers said isotonic fluid to said reservoir (23) when compressed. The bulb (6) is made of a material which may shrink when compressed by the fingers of the patient. While the bulb (6) may shrink in volume, it reverts back to its initial shape and volume when not compressed. The material of the bulb (7) would not allow the bulb expand beyond its initial volume even under the working pressure of the artificial sphincter (1).

As illustrated in FIG. 2A and FIG. 2B, the pump means (7) may have a three way valve (15) which is located in between the first port (13) and the second port (14) and which blocks fluid flow towards the occlusion means (20) when the bulb (6) is compressed. The three way valve (15) may have a ball (5) seated on a pervious seat (10) and biased by a spring (4) against said pervious seat (10).

A second tube (8) establishes the fluid connection in between the second port (14) of the pump means (7) and the distribution conduit (12) of the connection element (11). The fluid connection in between the occlusion means (20) and the first port (13) of the pump means (7) is established by a first tube (9) as illustrated in FIG. 1. Fluid contained in the pressure compensation balloon (24) may freely flow through the connection element (11) and pump means (7) towards the occlusion means (20) as there is no check valve which would block the flow of fluid from said pressure compensation balloon (24) towards the occlusion means (20). In other words, there is a free flow path for the isotonic fluid when flowing in the direction towards the occlusion means (20).

In an embodiment, the material of the pressure compensation balloon (24) is less elastic than the material of the fluid reservoir (23). In other words, the pressure compensation balloon (24) may be made of a thicker material so that pressure compensation balloon (24) may stretch less than the fluid reservoir (23) stretches. This provides that fluid reservoir (23) has an internal pressure which is larger than the internal pressure of the pressure compensation balloon (24). In this way, it is ensured that the flow of the isotonic fluid in between the pressure compensation balloon (24) and the fluid reservoir (23) is always towards the pressure compensation balloon (24).

The connection element (11) may have a protrusion (31) protruding towards the inner volume of the pressure compensation balloon (24) for preventing the material of the same clogging fluid entry. Likewise, the connection element (11) may have, on its other side, another protrusion (31) protruding towards the inner volume of the fluid reservoir for preventing the material of the same clogging fluid entry.

In the following paragraphs, the working scheme of the artificial sphincter (1) according to the preset invention will be described. The working scheme will be detailed by referral to FIG. 5, FIGS. 6A and 6B in which arrows indicate the flow direction of the isotonic fluid in the artificial sphincter (1). When the user activates the artificial sphincter (1) the occlusion means (20) occludes the body passage (18) and the artificial sphincter (1) reaches a steady state. During the steady state, the artificial sphincter (1) should entirely be full of the isotonic fluid having no gaps or air bubbles inside the system. In such a case, if there is zero abdominal pressure change, the isotonic fluid shall be steady and it shall not flow in between the various elements of the artificial sphincter (1).

As mentioned earlier, the idea underlying the present invention is to provide a free pathway for the isotonic fluid in between the pressure compensation balloon (24) and the occlusion means (20) so that a sudden abdominal pressure change may be simultaneously transmitted to the occlusion means.

FIG. 5 shows the flow stream of the fluid contained in the artificial sphincter during a moment of sudden abdominal pressure increase, which occurs such as when the patient to which an artificial sphincter (is) was implanted coughs or laughs etc. At such a moment, the pressure compensation balloon (24) immediately feels the pressure increase in the abdomen and shrinks in volume. The fluid contained in the pressure compensation balloon (24) first flows in the distribution conduit (12) and then towards the second port of the pump means (7) via the second tube (8). The fluid freely passes through the pump means (7) and reaches the occlusion means (20) via a first tube connecting the occlusion means (20) to the first port (13) of the pump means (7). Hence, the sudden increase in the abdominal pressure is immediately transmitted to the inflatable occlusion means (20). As the internal pressure of the inflatable occlusion means (20) increases with the incoming fluid flow from the pressure compensation balloon (24), it occludes the body passage (18) more effectively as compared to a steady state.

The connection element has a distribution conduit (12) which has, at its second end, a second check valve (26) blocking fluid flow from said fluid reservoir (23) to said pressure compensation balloon (24). During the moment of an abdominal pressure increase, the fluid leaving the pressure compensation balloon (24) would directly choose the direction to the second port (14) of the pump means via the second tube (8) and would not be directed to the fluid reservoir (23) because the fluid reservoir (23) is subject to the same abdominal pressure increase. The fluid reservoir (23) is subject to shrinking during an abdominal pressure increase and this increase results in transfer of isotonic fluid from the fluid reservoir (23) towards the pressure compensation balloon (24) via flow passage (28) of the connection element (11). As the fluid flow in the flow passage (28) is retarded by a flow retarder (27) located in the flow passage (28), the fluid contained in the fluid reservoir (23) gradually flows towards the pressure compensation balloon (24). Due to the fact that the second check valve (26) blocks fluid flow from said fluid reservoir to said pressure compensation balloon, the only flow path for the fluid contained in the fluid reservoir (23) is the unidirectional flow towards said pressure compensation balloon (24) through the flow passage (28).

Once the reason for the abdominal pressure increase ceases, i.e. the patient stops laughing or coughing, the extra amount of isotonic liquid transferred to the occlusion means (20) flow back to the fluid reservoir (23). The extra amount of fluid would not flow into the bulb (6) when passing through the pump means (7) due to the fact that the bulb (6) is already full of the isotonic fluid and its material is unable to bulge beyond its original volume.

When the patient intends to urinate or defecate, the occlusion means (20) shall be deflated in order to open the body passage (18). Assuming that the artificial sphincter is armed and in steady state, the patient needs to compress and release the bulb (6) a plurality of times. In every compression step, as depicted in FIG. 6A, the fluid contained in the bulb (6) would flow towards the fluid reservoir (23). On the other hand, in every expansion step of the bulb (6), as depicted in FIG. 6B, the fluid contained in the occlusion means (20) and in the pressure compensation balloon (24) flows through the bulb (6). Once the bulb (6) is repeatedly compressed and released, all the fluid contained in the occlusion means (20) would be transferred to the fluid reservoir (23) and the occlusion means (20) can be fully deflated. In the fully deflated state, the fluid contained in the occlusion means (20) is fully transferred to the fluid reservoir (23) since the bulb (6) cannot expand in size and continues to contain the same amount of fluid before the deflation cycle was started. Once the occlusion means (20) is fully deflated, the fluid contained in the same is transferred to the fluid reservoir which has an expanded size (23') as shown by broken lines in FIG. 6B.

For deflation of the occlusion means (20), the patient compresses the bulb (6) of the pump means (7) as illustrated in FIG. 6A. Once compressed, the isotonic fluid contained in the bulb (6) flows through the three way valve (15) towards the second port (14) of the pump means (7). During compression of the bulb, the three way valve (15) blocks the flow towards the first port (13) and hence the occlusion means (20). The isotonic fluid flow through the second tube (8) and enters in the distribution conduit (12). As the first check valve (30) located in the distribution conduit (12) block the flow towards the pressure compensation balloon (24), the flow enters in the fluid reservoir (23) and then passes gradually to the pressure compensation balloon (24) via the flow passage (28). The retarded flow from fluid reservoir (23) to the pressure compensation balloon (24) provides sufficient time for the patient for urination or defecation. This time is usually in the range of a few minutes before the fluid contained in the pressure compensation balloon (24) flows back to the occlusion means (20) and inflates the same for protection of the patient. The fluid flow which occurs automatically during said few minutes until said the occlusion means (20) is fully inflated is as illustrated in FIG. 5.

When the patient releases the bulb (6) of the pump means (7), the bulb reverts back to its original shape and volume. The fluid contained in the pressure compensation balloon (23) flows through the second tube (8) and enters the pump means (7) via the second port (14). The fluid then passes through the three way valve (15) and splits in two directions, one towards the bulb (6) and one towards the occlusion means (20) via the first port (13) of the pump means (7). Once the bulb (6) reverts it original size and shape, the fluid contained in the compensation balloon (24) is transferred only towards the occlusion means (20) in a retarded manner. This retardation is provided by the flow retarder (27) located in the flow passage (28) of the connection element (11). When ideally dimensioned, the flow retarder (27) provides that the occlusion means (20) reaches its full occlusion pressure in the range of 2-3 minutes after which time the patient is safe against incontinence.

During deflation of the artificial sphincter, the fluid contained in the occlusion means (20) flows towards the pump means (7) via the first tube (9). The fluid then moves through the three way valve (15) of the pump means (7) and leaves the pump means (7) via the second tube (8). The fluid enters the connection element (11) and flows through the distribution conduit (12) towards the fluid reservoir (23). Once the occlusion means (20) is fully deflated, the patient would have typically 2-3 minutes for urination or defecation. This is because the fluid transferred to the fluid reservoir (23) will automatically start passing to the pressure compensation balloon (24) through the flow passage (28) of the connection element (11). The flow retarder (27) located in the flow passage (28) retards the transfer of the fluid from the fluid reservoir (23) to the pressure compensation balloon (24). When ideally dimensioned the retarder (27) allows transfer of the received fluid in the range of 2-3 minutes, during which time the patient is allowed to urinate or defecate. Once the received amount of fluid is transferred to the pressure compensation balloon (24), the same fluid will start flowing through the first tube (8), the pump means (7) and the second tube (9) until it reaches the occlusion means (20) and the body passage (28) is automatically occluded.

The fluid reservoir (23) and the pressure compensation balloon (24) shall, in use, be implanted in the abdomen of the patient suffering incontinence. In such a case, the flow passage (28), which connects fluid reservoir (23) and the pressure compensation balloon (24) and which contains the flow retarder (27) shall normally be implanted in the abdomen of the patient in order to minimize the number of cuts in the abdominal area.

In the second and third embodiments of the invention, a connecting element (11) is not used. As shown in FIG. 7 and FIG. 8, the second tube (8) may split into two branches (8a, 8b) and the first check valve (30) may be located in the first branch (8a) whereas the second check valve (26) may be located in the second branch (8b). In this way, the first check valve (30) would ensure that the fluid coming from the second port (14) of the pump means would always enter fluid reservoir (23) and not the pressure compensation balloon (24). Likewise, the second check valve (26) located in the second branch (8b) would ensure that the fluid contained in the fluid reservoir (23) would only exit the reservoir through the flow passage (28) towards the pressure compensation balloon (24). As in the case of the first embodiment, during the inflation cycle of the occlusion means, fluid coming from the pressure compensation balloon (24) would be prevented from entering the fluid reservoir (23) and would always follow its free path towards occlusion means (20) via the pump means (7). This latter ensures that any pressure increase which may occur in the abdomen of the patient would immediately be felt by the occlusion means so that the body passage would be occluded with an increased working pressure of the occlusion means.

What is claimed is:

1. An artificial sphincter containing, in use, an isotonic fluid, artificial sphincter comprising:
    an inflatable occlusion means for occluding a body passage,
    a stretchable fluid reservoir,
    a pump having a first port in fluid communication with the inflatable occlusion means via a first tube and a second port in fluid communication with the fluid reservoir via a second tube for selectively transferring the isotonic fluid from the inflatable occlusion means to the reservoir to deflate the inflatable occlusion means so that the body passage may be opened;
    a pressure compensation balloon in fluid communication with the fluid reservoir via a flow passage, wherein, during use the pressure compensation balloon is configured to be implanted in an abdomen of a patient,
    a first check valve blocking fluid flow from the second port of the pump towards the pressure compensation balloon,
    a second check valve blocking fluid flow from the fluid reservoir towards the pressure compensation balloon,
    wherein, a fluid contained in the pressure compensation balloon is freely flowable towards the inflatable occlusion means and, in use, a pressure increase which occurs in the abdomen of the patient is instantly conveyed to the inflatable occlusion means.

2. The artificial sphincter according to claim 1, wherein the flow passage connecting the fluid reservoir and the pressure compensation balloon, comprises a flow retarder retarding the flow of fluid from the fluid reservoir to the pressure compensation balloon.

3. The artificial sphincter according to claim 1, wherein the pump has a bulb containing the isotonic fluid and the pump transfers the isotonic fluid to the fluid reservoir when compressed.

4. The artificial sphincter according to claim 3, wherein the pump has a three way valve located between the first port and the second port and the three way valve blocks the fluid flow towards the occlusion means when the bulb is compressed.

5. The artificial sphincter according to claim 3, wherein the pump has a three way valve for providing the fluid flow from the first port and the second port towards the bulb of the pump.

6. The artificial sphincter according to claim 1, wherein the inflatable occlusion means has an inflatable cushion having the body passage.

7. The artificial sphincter according to claim 1, wherein a material of the pressure compensation balloon is less elastic than a material of the fluid reservoir so that the fluid reservoir stretches more than the pressure compensation balloon.

8. The artificial sphincter according to claim 1, wherein each of the first check valve and the second check valve has a pervious seat and a ball which allows the fluid flow when the fluid forces the ball towards the pervious seat and blocks the fluid flow when a flow direction of the fluid is reversed.

9. The artificial sphincter according to claim 4, wherein the three way valve has a ball seated on a pervious seat and biased by a spring against the pervious seat.

10. The artificial sphincter according to claim 1, wherein the first check valve and the second check valve are formed in a connecting element.

11. The artificial sphincter according to claim 10, wherein the connection element has a protrusion protruding towards an inner volume of the pressure compensation balloon for preventing the clogging of a fluid entry.

12. The artificial sphincter according to claim 1, wherein the inflatable occlusion means is sized and shaped to occlude an anal or urethral canal of a human being.

* * * * *